United States Patent [19]

Carvais

[11] Patent Number: 4,902,513
[45] Date of Patent: Feb. 20, 1990

[54] ORAL SUSTAINED RELEASE MEDICAMENT

[76] Inventor: Jean Carvais, 201 Longview Dr., Alexandria, Va. 22314

[21] Appl. No.: 139,540

[22] Filed: Dec. 30, 1987

Related U.S. Application Data

[63] Continuation of Ser. No. 79,969, Jul. 31, 1987.

[51] Int. Cl.$^4$ ................................................ A61K 9/66
[52] U.S. Cl. ..................................... 424/455; 424/400; 514/937; 514/963
[58] Field of Search ............... 424/458, 455, 468, 489; 514/937, 963, 263, 305, 165

[56] References Cited

U.S. PATENT DOCUMENTS

| | | | |
|---|---|---|---|
| 3,005,755 | 10/1961 | Schoen | 514/263 X |
| 3,365,365 | 1/1968 | Butler et al. | 514/305 X |
| 4,085,214 | 4/1978 | Higuchi et al. | 514/263 |
| 4,478,822 | 10/1984 | Haslam et al. | 514/263 X |
| 4,717,713 | 1/1988 | Zatz et al. | 514/263 X |
| 4,761,288 | 8/1988 | Mezei | 424/450 |

FOREIGN PATENT DOCUMENTS 56-049315  5/1981  Japan ................................. 514/165

*Primary Examiner*—Thurman K. Page
*Attorney, Agent, or Firm*—Jones, Askew & Lunsard

[57] ABSTRACT

In a first aspect of the invention there is provided a dosage form for delivery of a fixed amount of a drug to provide a sustained release of said drug to a patient which comprises:

(a) a graduated container for accepting a liquid oral sustained release medicament, said graduated container being calibrated in units to permit an accurate total dosage of said drug; and (b) a liquid oral sustained release medicament capable of providing even blood levels of a drug in the bloodstream of a patient over a prolonged period of time, which comprises a suspension comprising microcapsules of said drug suspended in a saturated solution of said drug, the saturated level of said drug being maintained over a prolonged period of time for sustained release to the bloodstream and at a substantially constant level by means of the dissolution of the microcapsules into solution to replace the drug that leaves said solution, thereby maintaining the saturated level of drug in solution.

2 Claims, No Drawings

ORAL SUSTAINED RELEASE MEDICAMENT

This is a continuation application of U.S. application Ser. No. 079,969, filed July 31, 1987.

In a preferred aspect said graduated container is a cylinder having plural marking on at least one edge to denote the total dosage for said drug when said cylender is filled to a particular level with said liquid oral sustained release medicament.

In a further aspect said graduated container is a graduated eyedropper having plural markings on at least one edge to denote the total dosage for said drug when said graduated eyedropper is filled to a particular level with said liquid oral sustained release medicament.

In one embodiment of the invention, the sustained release medicament is insoluble of only slightly soluble in water and said suspension includes a non-aqueous solvent. As an example of such a drug may be mentioned aspirin.

In another embodiment of the invention, said liquid oral sustained release medicament is soluble in water and said suspension is an aqueous suspension. Examples of drugs within this embodiment of the invention include theophylline and quinidine sulfate.

In accordance with a second embodiment of the invention there is provided a liquid oral sustained release medicament capable of providing even blood levels of a drug in the bloodstream of a patient over a prolonged period of time, which comprises a suspension comprising microcapsules of said drug suspended in a saturated solution of said drug, the saturated level of said drug being maintained over a prolonged period of time for sustained release to the bloodstream and at a substantially constant level by means of the dissolution of the microcapsules into solution to replace the drug that leaves said solution, thereby maintaining the saturated level of drug in solution. This second aspect of the invention may be administered to a patient apart from the combination of the first aspect of the invention, for example, by measuring the amount of the drug with a spoon.

The following examples illustrate the invention:

EXAMPLE I

There is prepared a sustained-release aqueous liquid suspension of theophylline. The water vehicle is saturated with theophylline and has microcapsules containing theophylline core material suspended in the water.

Since one gram of theophylline is soluble in approximately 120 ml of water, each 5 cc of saturated aqueous solution contains 41.67 m of theophylline. By administering a suspension of microcapsules in a saturated aqueous vehicle it is possible to provide 200 mg of theophylline in 5 cc. This can be accomplished by incorporating into each 5 cc, suspended microcapsules containing about 158.33 mg of theophylline and 41.67 mg .of theophylline in solution. The quantity of theophylline in the microcapsules may be adjusted upward to compensate for the displacement of the saturated solution of theophylline.

A precise dosimeter can be included with the formulation package so that a precise dose may be administered, e.g., if the patient is to receive 200 mg every 12 hours, 5 ml is given or if the patient only required 100 mg every 12 hours, 2.5 ml may be given. This dosimeter may be a graduated cylinder or in the shape of an eyedropper, or other convenient form.

EXAMPLE II

Administration of the drug in accordance with Example I is illustrated as follows: An eight-year-old child who weighs 25 kilos (55 b) should achieve a blood level of approximately 15 mcg/ml when given a theophylline dose of 24 mg/kg/day or 300 mg (7.5 ml of the above solution) every 12 hours. Since it is unlikely that any patient woul d be "average," serum concentrations should be monitored and the dose adjusted accordingly. A broad dosage flexibility is provided by the invention since 0.5 ml increments of suspension (20 mg of theophylline) can be measured with a high degree of accuracy in conventional liquid dosimeters.

EXAMPLE III

Another example of a pharmaceutical formulation that would be used in this invention is quinidine sulfate for the treatment of ventricular arrhythmias. One gram of quinidine sulfate is soluble in 500 ml of water or 20 mg quinidine sulfate is soluble in 10 ml water. Thus a suspension containing 500 mg of quinidine sulfate in 10 ml/water could be formulated by dissolving 20 mg of quinidine sulfate in aqueous solution and suspending in the solution 480 mg of microencapsulated quinidine sulfate.

A daily dose per kilogram of quinidine base can be estimated form this simple formula:

$$\text{Daily Dose} = (c\!>\!-)(CL)(1440)/F$$

$c\!>\!-$ = average quinidine free base serum conoentration (mg/ml) desired.
$CL$ = total body drug clearance rate in ml/min/kg.
$1440$ = the number of minutes in a day.
$F$ = the percentage bioavailability.
For example:

$$\text{Daily Dosage} = \frac{(.002 \text{ mg/ml})(4.5 \text{ ml/min/kg})(1440 \text{ min})}{.99}$$

$$\text{Daily Dose} = \frac{12.96}{.99} = 13.1 \text{ mg/kg/day of free base}$$

This corresponds to 15.8 mg/kg/day of quinidine sulfate (13.1 mg/kg/day). A woman weighing 63 kilos would require a daily dose of approximately 995 mg or approximately 10 ml every 12 hours. If needed, dosage can be adjusted in 25 mg (0.5 ml) increments.

The gradual release of medication form the microcapsules in the liquid suspension, after they enter the gastrointestinal tract, at a relatively constant quantity per hour, enables plasma levels of the medication to be maintained at relatively constant levels. It also permits patients to take medication at less frequent intervals, thereby promoting compliance with the prescribed dosage regimen. For example, even though quinidine has a half-life of only 6.2 hours, it can be administered every 12 hours if incorporated into this system.

EXAMPLE IV

By following the same method of calculation as provided above for quinidine sulfate, a sustained release oral medication can be prepared for erythromycin, based upon the fact that 1 gm dissolves in 1000 ml of water.

EXAMPLE V

Utilization of the calculation techniques for quinidine sulfate, a sustained release oral medication can be prepared for Erythromycin ethylsuccinate, which is only slightly soluble in water but freely soluble in propylene glycol.

EXAMPLE VI

In place of the propylene glycol of Example V, there is substituted ethanol to make a saturated solution of Erythromycin ethylsuccinate.

EXAMPLE VII

By following the same method of calculation as provided above for quinidine sulfate, a sustained release oral medication can be prepared for Erythromycin estolate in propylene glycol.

EXAMPLE VIII

By following the same method of calculation as provided above for quinidine sulfate, a sustained release oral medication can be prepared for Erythromycin estolate in ethanol.

EXAMPLE IX

By following the same method of calculation as provided above for quinidine sulfate, a sustained release oral medication can be prepared for ampicillin, based upon the fact that 1 gram is soluble in 90 ml of water.

EXAMPLE X

By following the same method of calculation as provided above for quinidine sulfate, a sustained release oral medication can be prepared for Amoxicillin, as 1 gram is soluble in 370 ml of water.

EXAMPLE XI

Isosorbide dinitrate is only very slightly soluble in water, indicating an ethanolic medium. By following the same method of calculation as provided above for quinidine sulfate, a sustained release oral medication can be prepared for isosorbide dinitrate.

EXAMPLE XII

A propylene glycol suspension of isosorbide dinitrate is prepared as an alternate form for the sustained release form of Example XI.

EXAMPLE XIII

Tolubutamide is dissolved in an ethanolic medium. By following the same method of calculation as provided above for quinidine sulfate, a sustained release oral medication is prepared.

EXAMPLE XIV

A propylene glycol suspension of tolbutamide is prepared as an alternate form for the sustained release form of Example XIII.

EXAMPLE XV

By following the same method of calculation as provided above for quinidine sulfate, a sustained release oral medication can be prepared for prednisone, based upon the fact that 1 gm dissolves in 150 ml of water.

EXAMPLE XVI

A sustained release dosage form is made for the slightly water soluble hydrochlorothiazide.

EXAMPLE XVII

Probucol is practically insoluble in water, leading to the creation of an ethanol-based solvent system for a probucol dosage form.

EXAMPLE XVIII

A propylene glycol-based suspension is made for probucol replacing the ethanol.

EXAMPLE XIX

Atropine is soluble at the rate of one gram per 460 ml water. By following the same method of calculation as provided above for quinidine sulfate, a sustained release oral medication can be prepared.

The dosage delivery system of the invention provides for the formulation in the saturated solution to be immediately available for absorption and for the medication in the microcapsule reservoirs to be released at a relatively constant quantity per hour. This ensures substantially linear therapeutic blood levels once state has been achieved. Since steady states are usually achieved within five half-lives, the invention will make the use of potentially toxic drugs (e.g., theophylline) safer and permit less frequent dosage application, thereby ensuring patient compliance.

What is claimed is:

1. A liquid oral sustained release medicament capable of providing even blood levels of theophylline in the bloodstream of a patient over a prolonged period of time, which comprises a suspension comprising microcapsule of said theophylline suspended in a saturated solution of said theophylline, the sustained level of said theophylline being maintained over a prolonged period of time for sustained release to the bloodstream and at a substantially constant level by means of the dissolution of the microcapsule into solution to replace the theophylline that leaves said solution, wherein said liquid oral sustained release medicament is soluble in water and said suspension is an aqueous suspension.

2. A liquid oral sustained release medicament capable of providing even blood levels of theophylline in the bloodstream of a patient over a prolonged period of time, which comprises a suspension comprising microcapsules of said theophylline suspended in a saturated solution of said theophtlline the saturated level of said theophylline being maintained over a prolonged period of time for sustained release to the bloodstream and at a substantially constant level by means of the dissolution of the microcapsules into solution to replace the theophylline thatbleaves said solution, thereby maintaining the saturated level of theophylline in solution, wherein said liquid oral sustained release medicament in insoluble or slightly soluble in water and said suspension includes a non-aqueous solvent.

* * * * *